US00PP13880P29

(12) United States Plant Patent
Smith

(10) Patent No.: US PP13,880 P2
(45) Date of Patent: Jun. 17, 2003

(54) CHRYSANTHEMUM PLANT NAMED 'YOMINDY'

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/094,268

(22) Filed: Mar. 8, 2002

(51) Int. Cl.[7] ..... A01H 5/00
(52) U.S. Cl. ..... Plt./297

(58) Field of Search ..... Plt./297

*Primary Examiner*—Bruce R. Campell
*Assistant Examiner*—Annette Para
(74) *Attorney, Agent, or Firm*—C. A. Whealy

(57) ABSTRACT

A distinct cultivar of Chrysanthemum plant named 'Yomindy', characterized by its upright and mounded plant habit; freely branching habit; uniform and freely flowering habit; daisy-type inflorescences; purple-colored ray florets that do not fade with bright yellow-colored disc florets; and natural season flowering in late September in the Northern Hemisphere.

1 Drawing Sheet

BOTANICAL CLASSIFICATION/CULTIVAR DESIGNATION

*Chrysanthemum×morifolium* cultivar Yomindy.

BACKGROUND OF THE INVENTION

The present invention relates to a new and distinct cultivar of Chrysanthemum plant, botanically known as *Chrysanthemum×morifolium*, commercially known as a garden-type Chrysanthemum and hereinafter referred to by the name 'Yomindy'.

The new cultivar is a product of a planned breeding program conducted by the Inventor in Salinas, Calif. and Fort Myers, Fla. The objective of the breeding program is to create new garden-type Chrysanthemum cultivars having inflorescences with desirable inflorescence forms, attractive floret colors and good garden performance.

The new Chrysanthemum originated from a cross made in December, 1996, in Salinas, Calif., of an unnamed Chrysanthemum proprietary seedling selection, not patented, as the female, or seed, parent with the Chrysanthemum cultivar Empire Crown Jewel, disclosed in U.S. Plant Pat. No. 9,738, as the male, or pollen, parent. The new Chrysanthemum was discovered and selected by the Inventor as a single flowering plant within the progeny of the stated cross grown in a controlled environment in Fort Myers, Fla. in October, 1998. The selection of this plant was based on its desirable inflorescence form, attractive ray floret color and good garden performance.

Asexual reproduction of the new cultivar by terminal cuttings taken in a controlled environment in Fort Myers, Fla. since December, 1998, has shown that the unique features of this new Chrysanthemum are stable and reproduced true to type in successive generations.

SUMMARY OF THE INVENTION

The cultivar Yomindy has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yomindy'. These characteristics in combination distinguish 'Yomindy' as a new and distinct cultivar:

1. Upright and mounded plant habit.
2. Freely branching habit; dense and full plants.
3. Uniform and freely flowering habit.
4. Daisy-type inflorescences.
5. Purple-colored ray florets that do not fade with bright yellow-colored disc florets.
6. Natural season flowering in late September in the Northern Hemisphere.

In side-by-side comparisons conducted in Fort Myers, Fla., plants of the new Chrysanthemum differed from plants of the female parent, the unnamed selection, in the following characteristics:

1. Plants of the new Chrysanthemum flowered earlier than plants of the female parent under natural season conditions.
2. Ray florets of the new Chrysanthemum and the female parent differed in ray floret coloration.

Plants of the new Chrysanthemum are most similar to plants of the male parent, the cultivar Empire Crown Jewel. In side-by-side comparisons conducted in Fort Myers, Fla., plants of the new Chrysanthemum differed from plants of the cultivar Empire Crown Jewel in the following characteristics:

1. Plants of the new Chrysanthemum were fuller and more dense than plants of the cultivar Empire Crown Jewel.
2. Plants of the new Chrysanthemum flowered more uniformly than plants of the cultivar Empire Crown Jewel.
3. Ray florets of the new Chrysanthemum were darker in color than ray florets of the cultivar Empire Crown Jewel.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Yomindy'.

The photograph at the bottom of the sheet comprises a close-up view of typical inflorescences of the cultivar 'Yomindy'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Pendleton, S.C., under natural season conditions and practices which approximate those generally used in commercial garden-type Chrysanthemum production. One rooted cutting was planted in a 16.5-cm container in late July, 2002. Plants were not pinched, that is, the terminal apex was not removed to enhance branching. During the production of the plants, day temperatures ranged from 29 to 32° C. and night temperatures ranged from 16 to 21° C. Measurements and numerical values represent averages for typical flowering plants.

Botanical classification: *Chrysanthemum×morifolium* cultivar Yomindy.

Commercial classification: Daisy-type garden Chrysanthemum.

Parentage:

*Female, or seed, parent.*—Unnamed *Chrysanthemum×morifolium* proprietary seedling selection, not patented.

*Male, or pollen, parent.*—*Chrysanthemum×morifolium* cultivar Empire Crown Jewel, disclosed in U.S. Plant Pat. No. 9,738.

Propagation:

*Type.*—Terminal tip cuttings.

*Time to initiate roots.*—About four days at 21° C.

*Time to produce a rooted cutting.*—About ten days at 21° C.

*Root description.*—White, fine and fibrous.

*Rooting habit.*—Freely branching.

Plant description:

*Appearance.*—Perennial herbaceous daisy-type garden Chrysanthemum. Inverted triangle. Stems initially upright, then somewhat outwardly spreading giving a uniformly mounded appearance to the plant. Freely branching with lateral branches forming at every node.

*Plant height.*—About 31 cm.

*Plant diameter.*—About 46 cm.

*Lateral branches.*—Length: About 27 cm. Diameter: About 5 mm. Internode length: About 2.4 cm. Aspect: Upright and outwardly spreading. Texture: Pubescent. Color: Close to 146A.

*Foliage description.*—Leaf arrangement: Alternate. Length: About 4.3 cm. Width: About 3.4 cm. Apex: Cuspidate to mucronate. Base: Attenuate with truncate tendencies. Margin: Palmately lobed, sinuses mostly parallel. Texture: Both surfaces, pubescent; veins prominent on lower surface. Color: Young foliage upper surface: Darker than 147A. Young foliage lower surface: Slightly darker than 147B. Mature foliage upper surface: Slightly darker than 147A. Mature foliage lower surface: Closest to 147B. Venation, upper surface: 147A to 147B. Venation, lower surface: 147B to 147C. Petiole length: About 2.1 cm. Petiole diameter: About 2.5 mm. Petiole color: Upper surface: 147A to 147B. Lower surface: Closest to 147C.

Inflorescence description:

*Appearance.*—Daisy-type inflorescence form with elongated oblong-shaped ray florets. Inflorescences borne on terminals above foliage, arising from leaf axils. Disk and ray florets arranged acropetally on a capitulum. About 5 inflorescences per lateral.

*Flowering response.*—Under natural season conditions, plants flower in early October in the Northern Hemisphere and continue to flower for at least three weeks depending on weather conditions.

*Inflorescence bud (before showing color).*—Height: About 6 mm. Diameter: About 7.5 mm. Phyllary color: Darker than 143A.

*Inflorescence size.*—Diameter: About 5.4 cm. Depth (height): About 2.1 cm. Disc diameter: About 1.3 cm. Receptacle diameter: About 5.5 mm.

*Ray florets.*—Shape: Elongated oblong. Length: About 2.75 cm. Corolla tube length: About 4.5 mm. Width: About 6 mm. Apex: Acute, emarginate or dentate. Margin: Entire. Texture: Smooth, glabrous, satiny. Surface: Initially concave, then flat. Orientation: Initially upright, then about 60° from vertical. Number of ray florets per inflorescence: About 51 in about two rows. Color: When opening, upper surface: Close to 155D, heavily overlain with 70A to 71A; towards base, close to 155D. When opening, lower surface: Close to 155D, underlain with 77A. Opened inflorescence, upper surface: Close to 155D, overlain with 70A to 71A; towards base, close to 155D; with subsequent development, less purple coloration. Opened inflorescence, lower surface: Close to 155D, underlain with 77A.

*Disc florets.*—Shape: Tubular, apex dentate. Length: About 6 mm. Width: Apex: About 2 mm. Base: About 1 mm. Number of disc florets per inflorescence: About 110. Color: Immature: 154A to 9A. Mature: Apex: 9A. Mid-section: 154D. Base: 155D.

*Peduncle.*—Aspect: Flexible, angled about 45 to 50° from the stem. Length: First peduncle: About 5.7 cm. Fourth peduncle: About 7.3 cm. Diameter: About 3 mm. Texture: Pubescent. Color: Close to 146A.

*Reproductive organs.*—Androecium: Present on disc florets only. Anther color: 9A. Pollen: Moderate. Pollen color: 15A. Gynoecium: Present on both ray and disc florets.

*Seed.*—Seed production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 40° C.

It is claimed:

1. A new and distinct cultivar of Chrysanthemum plant named 'Yomindy', as illustrated and described.

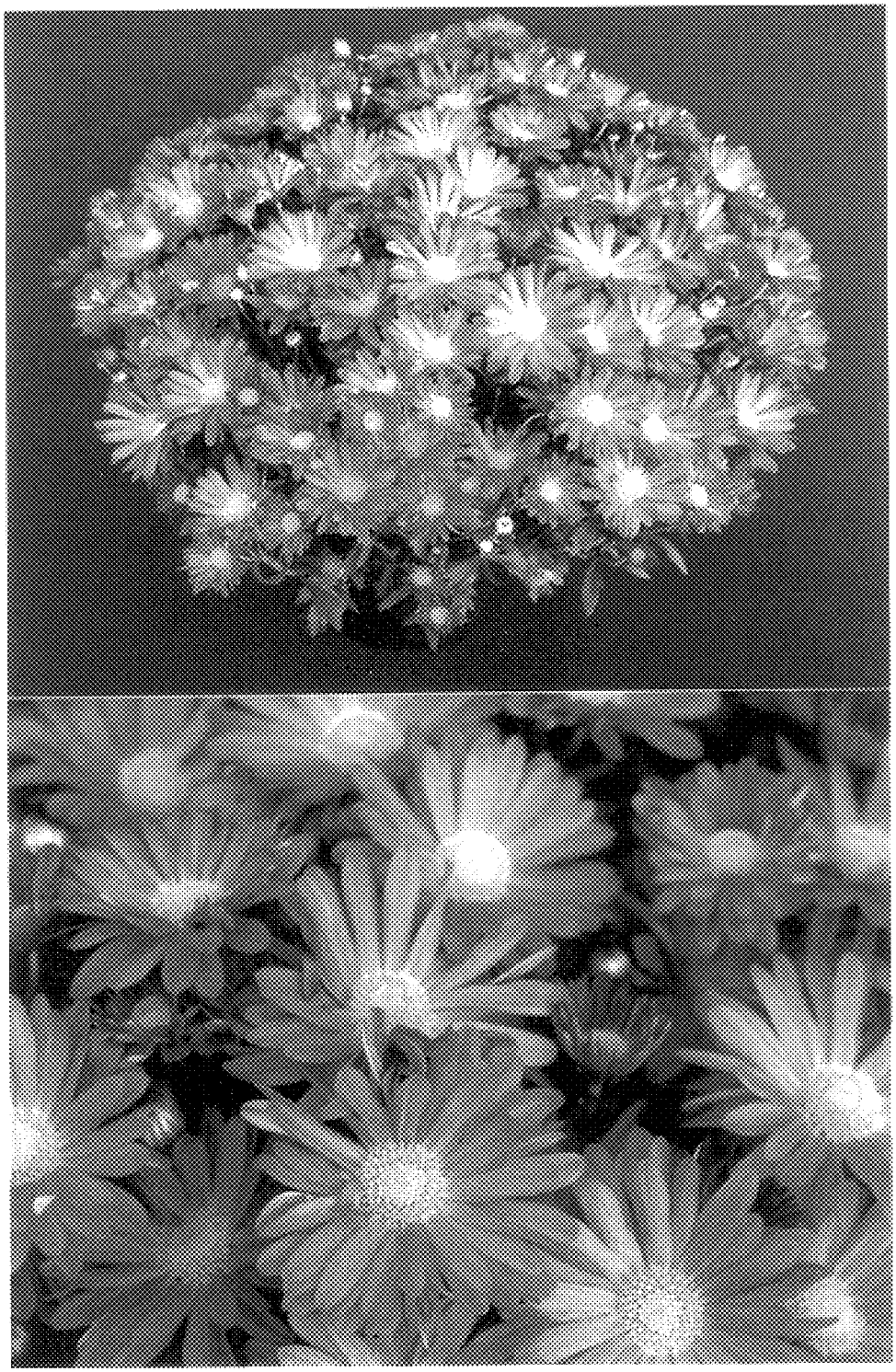

* * * * *